United States Patent [19]

Colas et al.

[11] Patent Number: 4,777,277
[45] Date of Patent: Oct. 11, 1988

[54] ORGANOSILICON SULPHOSUCCINATES

[75] Inventors: André R. L. Colas, Glashutten, Fed. Rep. of Germany; Franck A. D. Renauld, Barry, United Kingdom

[73] Assignee: Dow Corning, Ltd., Barry, Wales

[21] Appl. No.: 163,597

[22] Filed: Mar. 3, 1988

[30] Foreign Application Priority Data

Mar. 14, 1987 [GB] United Kingdom ............... 8706093

[51] Int. Cl.$^4$ .......................... C07F 7/10; C07F 7/08
[52] U.S. Cl. ................... 556/419; 556/428
[58] Field of Search .................. 556/419, 428

[56] References Cited

U.S. PATENT DOCUMENTS

| | | | |
|---|---|---|---|
| 2,589,446 | 3/1956 | Sommer | 556/428 |
| 2,928,858 | 3/1960 | Morehouse | 556/419 |
| 3,187,033 | 6/1965 | Nitzsche et al. | 260/448.2 |
| 3,328,449 | 7/1967 | Haluska | 260/448.2 |
| 3,507,897 | 4/1970 | Kanner | 260/448.2 |
| 3,660,452 | 5/1972 | Morehouse | 260/448.2 |
| 4,503,242 | 3/1985 | Plueddemann | 556/419 X |
| 4,717,498 | 1/1988 | Maxon | 556/428 X |

Primary Examiner—Paul F. Shaver
Attorney, Agent, or Firm—Marc C. Pawl

[57] ABSTRACT

Silanes and organosiloxanes having the group $$\equiv \text{SiQYCCHCH}_2\text{COO}^-\text{Na}^+$$
$$\underset{\text{OSO}_3^-\text{Na}^+}{\overset{\parallel \;\;|}{}}$$

wherein Q represents an olefinically-saturated divalent hydrocarbon group and Y represents —O— or —NH—.

They can be prepared by the reaction of sodium sulphite or sodium bisulphite on the ester or amide $$\equiv \text{SiQY}\overset{O}{\overset{\parallel}{C}}-\text{CH}=\text{CH}\overset{O}{\overset{\parallel}{C}}\text{OH}$$

and are useful as surface active agents.

5 Claims, No Drawings

ORGANOSILICON SULPHOSUCCINATES

This invention relates to sulphonated organosilicon compounds and is particularly concerned with novel organosilicon sulphosuccinate compounds and a process for their preparation.

Organosilicon compounds having substituents which contain sulphonate ($-SO_3^-Na^+$) groups are known. Such compounds are described in British Pat. Nos. 1 270 977, 1 005 872, 1 030 888 and 1 198 096. Various methods of preparation of the sulphonated compounds are disclosed in said patents including the reaction of epoxysiloxanes with a primary or secondary amine sulphonate or with sodium bisulphite, the reaction of a mercaptoethyl silicon compound with sodium methoxide and further reaction of the product with a hydroxypropane sulphonic acid and the reaction of an organosilicon compound having unsaturated substituents with an alkali metal sulphite or pyrosulphite. According to the present invention there are provided novel organosilicon compounds which are (A) organosilanes represented by the general formula

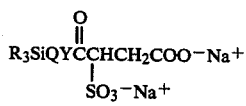

or (B) organosiloxanes having in the molecule at least one unit represented by the general formula

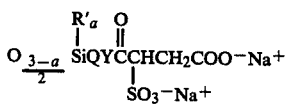     (i)

any other units present in the organosiloxanes being those represented by the general formula

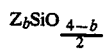     (ii)

wherein each R and each R' represents a methyl, ethyl or phenyl group, Q represents an olefinically saturated divalent hydrocarbon group having from 2 to 10 carbon atoms, Y represents $-O-$ or $-NH-$, Z represents a hydrogen atom or a monovalent hydrocarbon group having from 1 to 18 carbon atoms, a has a value of 0, 1 or 2 and b has a value of 0, 1, 2 or 3 provided that there is present in said organosiloxane molecule at least one substituent selected from R' and Z, Z being other than hydrogen.

In the general formulae of the silanes and organosiloxanes of this invention each R and each R' may be methyl, ethyl or phenyl but from the standpoint of commercial availability are preferably methyl or phenyl. The group Q has from 2 to 10 carbon atoms. It may be an alkylene group, for example $-CH_2CH_2-$, $-(CH_2)_4-$ and $-CH_2CH_2C(CH_3)_2-$, or it may be an arylene, aralkylene or alkarylene group, for example, phenylene, tolylene, xylylene or phenylpropylene. Preferably Q represents the group $-(CH_2)_3-$ or the group $-CH_2CHCH_3CH_2-$. The substituent Z may be a hydrogen atom or any monovalent hydrocarbon group having from 1 to 18 carbon atoms. Examples of Z substituents are, therefore, alkyl groups e.g. methyl, ethyl, propyl, trimethylpentyl, dodecyl and tetradecyl; alkenyl groups e.g. vinyl and allyl; and aryl, alkaryl and aralkyl groups e.g. phenyl, 2-phenylpropyl and tolyl. When the intended use of the organosiloxanes is related to their surface active properties it is generally preferred that the Z substituents are methyl groups.

The organosiloxane should have at least one silicon-bonded organic group in addition to the specified sulphosuccinate group. Therefore, at least one R' and/or Z group should be present, Z being other than hydrogen.

The organosiloxanes of this invention have in the molecule at least one unit falling within general formula (i). They may be homopolymers consisting only of units (i) or they may be copolymers containing both units (i) and units falling within general formula (ii). The organosiloxanes may vary in molecular size from the disiloxanes to high molecular weight homopolymers and copolymers and may vary in consistency from liquids to solids. The silanes are solids. The preferred organosiloxanes are those which are linear or substantially linear in form, that is polydiorganosiloxanes comprising units (i) and optionally (ii) wherein a is 1 or 2 and b is 2 or 3.

The organosilicon compounds of this invention can be prepared by the reaction in the presence of water and basic substance of (1) an organosilicon compound which is (C) a silane represented by the general formula

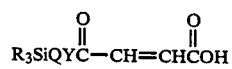

or (D) an organosiloxane having in the molecule at least one unit represented by the general formula

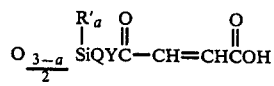

any other units present being those represented by the general formula

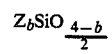

wherein R, R', Q, Y, Z, a and b are as hereinbefore defined, with (2) sodium bisulphite.

The organosilicon compounds (A) which are employed in the process of this invention can be readily obtained by the reaction of maleic acid or maleic anhydride with a silane or organosiloxane having a hydroxy hydrocarbon substituent ($Y = -O-$) or an aminohydrocarbon substituent ($Y = -NH-$), for example,

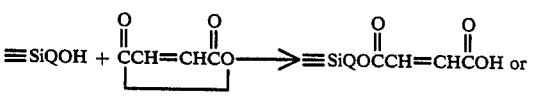

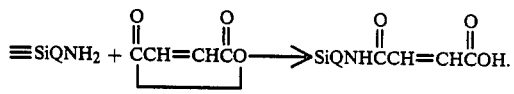

The hydroxyhydrocarbon-substituted and aminohydrocarbon-substituted organosilicon compounds are known substances and can be prepared by well established processes.

Preparation of the silanes and organosiloxanes of this invention may be carried out by bringing together (1), (2), water and a basic substance. Suitable bases are those which are capable of reacting with the carboxyl groups in (1) to form the salt. Preferred bases are the alkali metal salts, in particular hydroxides and carbonates of sodium and potassium. Most preferred is sodium hydroxide which if desired, can also function as precursor in the formation of reactant (2), as hereinafter described. Reactant (2) may be incorporated into the reaction mixture per se or it may be formed in situ by incorporating suitable precursors which are converted to (2) under the reaction conditions, for example sodium metabisulphite which forms sodium bisulphite on contact with water. Sodium sulphite forms both a base (NaOH) and (2) and may thus also be used. The process of this invention may be performed by simply mixing (1), (2), water and a base. Preferably, however, the process is carried out such that reactant (1) is first converted to the salt by reaction with the base. Such conversion results in a more homogenous reaction mixture and thus more efficient performance of the sulphonation reaction.

The proportion of (2) employed relative to (1) may vary widely depending on the number of ester or amide groups to be converted to sulphosuccinate groups in the product. Generally the sodium bisulphite will be employed in metathetical quantities, that is one mole of the bisulphite per ester or amide group.

Some reaction between (1) and (2) may occur at normal ambient temperatures (about 22° C.). It is preferred, however, to expedite the reaction by the use of elevated temperatures, conveniently from about 40° C. to the reflux temperature of the reaction mixture. Although the reaction may be carried out in the absence of a solvent it is preferable to employ a solvent to assist in obtaining a homogeneous reaction mixture. Suitable for this purpose are the polar solvents, particularly the lower aliphatic alcohols, for example methyl alcohol and ethyl alcohol.

The organosilicon compounds of this invention possess both hydrophobic and hydrophilic groups in the same molecule and exhibit significant surface active properties. They are thus useful in aqueous systems as emulsifying agents, foaming agents and are also effective in breaking aqueous emulsions of crude oil.

The following example in which Me signifies the methyl group illustrate the invention.

EXAMPLE 1

The copolymer

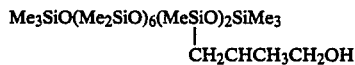

was prepared by the addition of methyl-2-propen-3-ol to the corresponding methylhydrogen polysiloxane in the presence of a platinum catalyst.

43.5 g (0.05 mole) of this copolymer were mixed with maleic anhydride (9.8 g, 0.1 mole) and toluene (40 g) and the mixture heated under nitrogen to 110° C. for 90 minutes. The toluene was then removed by volatilisation to leave the maleic ester polysiloxane.

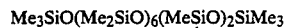
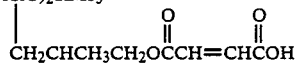

The maleic ester thus obtained (42.64 g, 0.04 mole) was dissolved in methyl alcohol (40 g) and a normal solution (74 ml) of sodium hydroxide added to neutral pH. Sodium metabisulphite (7.03 g) was then added and the mixture heated to 81° C. for 3 hours. When the volatiles were stripped from the reaction product after this time a white solid was obtained having the formula

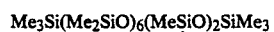
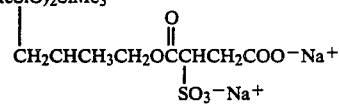

When 2 g of this solid were dissolved in water (100 ml) a solution was obtained having a surface tension of 25.1 dynes cm$^{-1}$.

EXAMPLE 2

Maleic anhydride (4.9 g, 0.05 mole) dissolved in toluene (50 ml) was added to γ-aminopropylheptamethyltrisiloxane (13.95 g, 0.05 mole) and the mixture heated to 50° C. for 1 hour. The toluene was then removed by distillation to leave the maleic amide polysiloxane

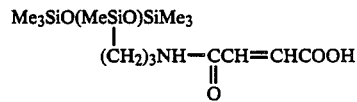

7.54 g of this polysiloxane were suspended in water (10 g) by stirring and 20 ml of normal sodium hydroxide solution added to render the mixture neutral (pH 7). To this mixture was then added a solution of sodium bisulphite (2.08 g) in water (15 ml) and the resulting mixture heated to 49° C. for 2 hours. When the water was removed by evaporation a white solid remained having the formula

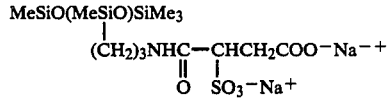

When 0.2 g of this solid was dissolved in 100 ml of water a clear solution was obtained having a surface tension of 20.6 dynes cm$^{-1}$.

EXAMPLE 3

The disiloxane (Me$_2$R″Si)$_2$O, in which R″ represents

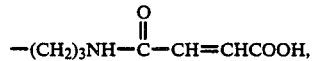

(22.2 g, 0.05 mole) was charged to a flask equipped with stirrer, reflux condenser, thermometer and nitrogen inlet together with methyl alcohol (10 g). Normal NaOH solution (100 ml) was then added until pH7. Upon completion of the addition the mixture was stirred for 0.5 hour and Na$_2$S$_2$O$_5$ (9.5 g, 0.025 mole) added. The flask was then heated with stirring to 45°-50° C. for 3 hours and the reaction followed by titration (KI/KIO$_3$) which indicated that 95% of the NaHSO$_3$ present was consumed during the 3 hour period.

Acetone was added to the cooled reaction mixture and the desired product

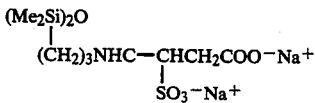

was precipitated as a white powder.

EXAMPLE 4

Employing the procedure of Example 1 24 g of the siloxane

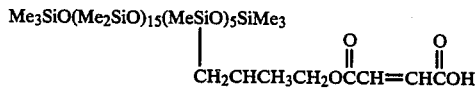

was reacted at 60° C. for 4 hours with 4.08 g of Na$_2$S$_2$O$_5$ in the presence of 50 ml normal NaOH and 10 g methyl alcohol.

The product

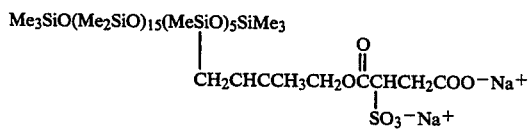

contained 7.1% by weight of Na (Theory 7.53%).

That which is claimed is:

1. Organosilicon compounds which are (A) organosilanes represented by the general formula

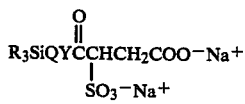

or (B) organosiloxanes having in the molecule at least one unit represented by the general formula

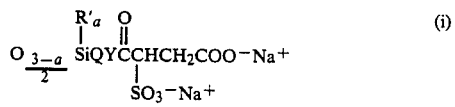

any other units present in the organosiloxanes being those represented by the general formula

where each R and each R' represents a methyl, ethyl or phenyl group, Q represents an olefinically saturated divalent hydrocarbon group having from 2 to 10 carbon atoms, Y represents —O— or —NH—, Z represents a hydrogen atom or a monovalent hydrocarbon group having from 1 to 18 carbon atoms, a has a value of 0, 1 or 2 and b has a value or 0, 1, 2 or 3, provided that there is present in said organosiloxane molecule at least one substituent selected from R' and Z, Z being other than hydrogen.

2. Organosilicon compounds as claimed in claim 1 wherein Z is methyl.

3. A process for the preparation of an organosilicon compound of the kind claimed in claim 1 which comprises reacting in the presence of water and a basic substance (1) an organosilicon compound which is (C) a silane represented by the general formula

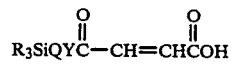

or (D) an organosiloxane having in the molecule at least one unit represented by the general formula

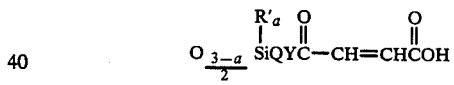

any other units present being those represented by the general formula

wherein R, R', Q, Y, Z, a and b are as defined in claim 1 and provided that there is present in said organosiloxane molecule at least one substituent selected from R' and Z, Z being other than hydrogen, and (2) sodium bisulphite.

4. A process as claimed in claim 3 wherein the reaction mixture also contains an aliphatic alcohol.

5. A process as claimed in claim 3 which also includes the step of adding a reagent which converts (1) to its sodium salt.

* * * * *